United States Patent [19]

Ito et al.

[11] Patent Number: 5,525,334
[45] Date of Patent: Jun. 11, 1996

[54] METHOD FOR VASCULAR EMBOLIZATION

[75] Inventors: Shoji Ito; Yuji Matsumaru; Takashi Hirano; Shinichi Ohashi, all of Tsukuba, Japan

[73] Assignee: Japan as represented by Director General of Agency of Industrial Science and Technology, Japan

[21] Appl. No.: 408,395

[22] Filed: Mar. 22, 1995

[30] Foreign Application Priority Data

Jun. 3, 1994 [JP] Japan .................................. 6-145533

[51] Int. Cl.⁶ ................................................. A61K 31/785
[52] U.S. Cl. ........................ 424/78.35; 514/824; 514/834
[58] Field of Search ...................... 526/303.1; 424/78.08, 424/78.35; 514/824, 930, 834

[56] References Cited

U.S. PATENT DOCUMENTS 4,732,930  3/1988  Tanaka et al. ...................... 526/303.1
5,202,352  4/1993  Okada et al. ........................... 514/475

*Primary Examiner*—Peter F. Kulkosky
*Attorney, Agent, or Firm*—Wenderoth, Lind & Ponack

[57] ABSTRACT

Proposed is a method for vascular embolization of the blood vessel of a patient by introducing an aqueous solution of a specific thermosensitive polymer, which is liquid at low temperatures but causes coagulation when heated up to the body temperature of the patient, into the blood vessel followed by in situ heating of the solution. The thermosensitive polymer found to be suitable for the purpose is a homopolymer or copolymer of an N-substituted (meth) acrylamide monomer having a specified intrinsic viscosity in tetrahydrofuran and gives an aqueous solution capable of exhibiting phase transition from a liquid to a coagulate at a transition temperature of 10° to 37°.

5 Claims, 1 Drawing Sheet

METHOD FOR VASCULAR EMBOLIZATION

BACKGROUND OF THE INVENTION

The present invention relates to a method for vascular embolization or, more particularly, to a method for vascular embolization in which a liquid embolizing agent, which can be coagulated at the body temperature, is introduced into the blood vessel of a patient so as to prevent bleeding from the open end of the blood vessel or to facilitate cure of disordered blood vessel without undertaking a surgical procedure with embolization of the disordered blood vessel by the subsequent coagulation of the embolizing agent.

As a consequence of the remarkable progress in the medical science and technology in recent years, intravascular surgery is now frequently undertaken as a therapeutic means from inside of blood vessels as an application of the radiological technology for angiography. In conducting such intravascular surgery, it is essential to establish a means for the vascular embolization using a vascular embolizing agent by which the blood vessel to be subjected to the surgery is embolized to prevent bleeding from the open end thereof. Further, it is expected that the disordered blood vessel can be cured without undertaking ordinary surgical procedure by embolizing the disordered blood vessel.

A vascular embolizing agent above mentioned, which is a liquid capable of being coagulated or converted into a non-flowable mass after injection into the blood vessel of the patient, must satisfy several requirements, i.e., that it be a liquid suitable for smooth injection into blood vessels without difficulty, that the length of time taken for coagulation in the blood vessel of a living body can be controlled within a wide range, that it be stable in and non-toxic against human body, that it can withstand a sterilization treatment without causing denaturation, that the coagulate of the agent can be re-dissolved, for example, in the event of inadvertent trouble due to embolization of a normal blood vessel to regain blood circulation, that it be opaque to X-rays in order to facilitate detection of the location where vascular embolization has taken place and so on. However, no vascular embolizing agent is available which can satisfy all of these requirements.

For example, vascular embolizing agents heretofore known include a polymerizable monomeric compound such as n-butyl cyanoacrylate which can be converted into a polymer after being injected into the blood vessel of a patient and a solution of a polymer in an organic solvent, such as ethyl alcohol and dimethyl sulfoxide, from which, when injected into a blood vessel, the solvent is absorbed by diffusion into the tissue of the blood vessel to leave the polymeric material. Examples of the polymer suitable for this purpose include copolymers consisting of ethylene and vinyl alcohol moieties soluble in dimethyl sulfoxide, polyvinyl acetate soluble in ethyl alcohol, a commercial product sold under a tradename of Eudragit (copolymer of (meth) acrylic monomers, a product by Röhm Pharma Co., Germany) soluble in ethyl alcohol and so on.

The above mentioned butyl cyanoacrylate acts as an adhesive when it is polymerized so that the use thereof as a vascular embolizing agent involves a risk of complications to the patient. The solution-type agents of the latter class are unavoidably accompanied by troubles due to absorption of the organic solvent in the living body. For example, ethyl alcohol is liable to cause dermatopathy within the blood vessel and dimethyl sulfoxide has a problem of, besides the physiological effects on the living body, solubility to various polymers so that catheters of a certain polymer are dissolved by the dimethyl sulfoxide solution.

Thus, the liquid vascular embolizing agents heretofore proposed are each not free from the disadvantages due to the risk of very harmful side effects and the various troubles for which the organic solvents are responsible.

SUMMARY OF THE INVENTION

The present invention accordingly has an object to provide a novel and improved method for vascular embolization by use of a liquid vascular embolizing agent, which method is free from the above described problems and disadvantages in the vascular embolizing methods by the use of a conventional vascular embolizing agent.

Thus, the method of the present invention for vascular embolization of a blood vessel of a patient comprises the steps of:

(a) injecting, into the blood vessel of the patient, an aqueous solution containing from 0.5% to 50% by weight of a thermosensitive polymer consisting of the monomeric units comprising a monomeric moiety represented by the general formula $$+CH_2-CR^1(-CO-NR^2R^3)+, \qquad (I)$$ 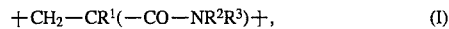

in which $R^1$ is a hydrogen atom or a methyl group, $R^2$ is a hydrogen atom, an alkyl group or an alkoxy-substituted alkyl group and $R^3$ is an alkyl group or an alkoxy-substituted alkyl group, having an intrinsic viscosity $[\eta]$ in the range from 0.01 to 6.0 dl/g in tetrahydrofuran at 27° C. and having a transition temperature for coagulation of the aqueous solution by the phase transition of the polymer into a coagulate within a range from 10° to 37° C., at a temperature lower than the transition temperature; and (b) heating the aqueous solution of the thermosensitive polymer inside of the blood vessel up to a temperature higher than the transition temperature either externally or by the body temperature of the patient.

The above mentioned monomeric moiety of the general formula (I) is obtained by the polymerization of an N-substituted (meth) acrylamide or copolymerization of a monomeric mixture consisting of the same monomer and one or more of other ethylenically unsaturated monomeric compounds, of which the fraction of the N-substituted (meth) acrylamide monomer is at least 10% by moles or, preferably, at least 30% by moles or, more preferably, at least 50% by moles.

DETAILED DESCRIPTION OF THE PREFERRED EMBODIMENTS

Figure 1:
FIG. 1 is a microscopic photograph of a section of the renal tissue of a rabbit showing the arteries of the kidney embolized according to the inventive method.

As is described above, the most characteristic feature of the inventive method consists in the use of an aqueous solution of a specific thermosensitive polymer which is a liquid at low temperatures but converted into a coagulate when the solution is heated at a temperature to exceed a certain transition temperature specific to the respective polymer within the range of 10° to 37°. Namely, an aqueous solution of the polymer is injected into the blood vessel of a patient at a temperature lower than the transition temperature followed by subsequent heating of the solution in the blood vessel up to a temperature higher than the transition temperature of the polymer so as to form a coagulate in situ. Since the phase transition of the polymer is a reversible process, the coagulate once formed in the blood vessel can easily be re-dissolved by lowering the temperature. Needless to say, the polymer is absolutely inert to the living body, not causing problems due to intoxication or other side effects.

The thermosensitive polymer used in the inventive method has a molecular structure comprising the monomeric moiety represented by the above given general formula (I). The monomeric moiety of the formula (I) can consist of a single kind of the monomeric units of the formula or can consist of two kinds or more of the monomeric units each within the definition of the formula. Further, while the monomeric moiety of the general formula (I) is derived from an N-substituted (meth) acrylamide monomer, it is optional that the polymer is prepared by the copolymerization of a monomer mixture consisting of the N-substituted (meth) acrylamide monomer and one or more kinds of other ethylenically unsaturated comonomers provided that the fraction of the N-substituted (meth) acrylamide monomer to give the monomeric units of the formula (I) in the monomer mixture is at least 10% by moles or, preferably, at least 30% by moles or, more preferably, at least 50% by moles. At any rate, it is essential that the polymer exhibits a thermoreversible phase transition in an aqueous solution between hydrophilicity at low temperatures and hydrophobicity at elevated temperatures with a transition temperature therebetween. In view of the fact that the body temperature of patients is usually around 37° C. and a difficulty is encountered when the temperature of the injectant solution is too low, the transition temperature is desirably somewhere between 10° and 37° C.

As a means to determine the transition temperature of the thermosensitive polymer, a turbidimetric measurement of an aqueous solution of the polymer can be undertaken. Thus, the transmission of light of 500 nm wavelength through a 1% by weight aqueous solution of the polymer is measured in a spectrophotometer equipped with a temperature controller under increasing or decreasing of the temperature at a rate of 1° C./minute and the temperature $T_L$, at which the light transmission is just a half of the value at a temperature of 10° C. or lower, is taken as a measure of the transition temperature.

Besides the above mentioned limitation in the transition temperature, it is important that the thermosensitive polymer has an average molecular weight corresponding to an intrinsic viscosity at 27° C. in tetrahydrofuran in the range from 0.01 to 6.0 dl/g or, preferably from 0.1 to 2.0 dl/g. When the intrinsic viscosity of the polymer is too low indicating an unduly low average molecular weight thereof, the coagulate of the polymer solution to embolize the blood vessel would be too soft to withstand the blood pressure or other external forces so that no satisfactory embolizing effect can be obtained. When the intrinsic viscosity of the polymer is too high corresponding to an unduly high average molecular weight thereof, on the other hand, difficulties or troubles are encountered in the preparation of an aqueous solution of the polymer in an adequate concentration due to the decrease in the water-solubility of the polymer or in the injection of the aqueous polymer solution into the blood vessel due to the unduly high viscosity of the solution.

The concentration of the thermosensitive polymer in the aqueous injectant solution is in the range from 0.5% to 50% by weight or, preferably, from 1% to 30% by weight. The coagulate or the gel formed from the polymer solution by increasing the temperature would be too soft or still flowable so that the coagulate cannot withstand the blood pressure not to exhibit a vascular embolizing effect. A polymer solution of a concentration to exceed the above mentioned upper limit can hardly be prepared or, even if such a high-concentration solution could ever be prepared, difficulties are encountered in the injection of the solution into the blood vessel due to the unduly high viscosity of the solution.

The above described thermosensitive polymer can be prepared by the polymerization of an N-substituted (meth) acrylamide monomer represented by the general formula

$$CH_2=CR^1-CO-NR^2R^3, \qquad (II)$$

in which each symbol has the same meaning as defined before. It has been found that some of the N-substituted (meth)acrylamide monomers to meet the above mentioned definition can be polymerized alone to give a homopolymer which in itself has a transition temperature within the above mentioned desirable range of 10° to 37° C. Examples of such a monomer, referred to as the first group monomer hereinafter, include: N-n-propyl acrylamide; N-n-propyl methacrylamide; N-isopropyl acrylamide; N-isopropyl methacrylamide; N,N-diethyl acrylamide; N-methyl-N-n-propyl acrylamide; N-methyl-N-isopropyl acrylamide; N-(3-ethoxypropyl) acrylamide; N-(3-ethoxypropyl) methacrylamide; N-(2-ethoxyethyl) acrylamide; N-(1-methyl-2-methoxyethyl) acrylamide; N-(3-methoxypropyl) acrylamide; N-(3-methoxy-propyl) methacrylamide; N-(3-isopropoxypropyl) acrylamide; N-(3-isopropoxypropyl) methacrylamide; N-(2-isopropoxyethyl) acrylamide; N-(2-isopropoxyethyl) methacrylamide; N-cyclopropyl methacrylamide; N-(1-methoxymethyl propyl) acrylamide; N-(1-methoxymethyl propyl) methacrylamide; and the like. These (meth) acrylamide monomers can be polymerized either singly to give a homopolymer or as a combination of two kinds or more to give a copolymer according to need. Besides the above named (meth) acrylamide monomers, N-tetrahydrofurfuryl acrylamide, N-tetrahydrofurfuryl methacrylamide, N-(3-morpholinopropyl) acrylamide, N-cyclopropyl methacrylamide, N-1-methoxymethylpropyl acrylamide, N-1-methoxymethylpropyl methacrylamide and the like can be used as the first group monomer.

It has been discovered that, when the thermosensitive polymer is a copolymer of two kinds or more of the (meth) acrylamide monomers, the transition temperature of the copolymer can be calculated from the transition temperatures of the individual homopolymers prepared from the respective comonomers and the molar fraction of the respective comonomers in the monomer mixture according to the additivity rule. This fact provides a means to freely control the transition temperature of the thermosensitive polymer by adequately selecting the kinds and the molar fractions of the comonomers in the monomer mixture to be copolymerized (see, for example, Polymer Preprints, Japan, volume 40, No. 3, page 1083, 1991).

The above mentioned additivity rule relating to the transition temperature of a copolymer prepared from different kinds of comonomers leads to a possibility that even a (meth) acrylamide monomer expressed by the above given general formula (II), which alone cannot give a homopolymer having a transition temperature of 10° to 37° C., can be used as one of the comonomers combined to give a copolymer having a transition temperature of 10° to 37° C. For example, a (meth) acrylamide monomer, which alone gives a homopolymer having a transition temperature lower than 10° C., referred to as the second group monomer hereinafter, and a (meth) acrylamide monomer, which alone gives a homopolymer having a transition temperature higher than 37° C., referred to as the third group monomer hereinafter, can be copolymerized to give a copolymer having a transition temperature of 10° to 37° C. provided that the molar mixing proportion of the comonomers is appropriate. Likewise, combinations of the second group monomer and the first group monomer or combinations of the third group monomer and the first group monomer are also suitable provided that the kinds and molar fractions of the respective comonomers are adequately selected.

Examples of the second group monomer, i.e. the monomer giving a homopolymer having a transition temperature lower than 10° C., include N-ethyl acrylamide, N-cyclopropyl acrylamide and N-methyl-N-ethyl acrylamide while examples of the third group monomer, i.e. the monomer giving a homopolymer having a transition temperature higher than 37° C., include N-(2-ethoxyethyl) acrylamide and N-(2,2-dimethoxyethyl) acrylamide.

Furthermore, it is not always necessary that the thermosensitive polymer used in the invention consists of the monomeric units of the general formula (I) alone but the thermosensitive polymer is a copolymer of an N-substituted (meth) acrylamide monomer which alone gives a homopolymer having a transition temperature of 10° to 37° C. in water and one or more of other ethylenically unsaturated monomeric compounds, from which no thermosensitive homopolymer can be obtained, as a comonomer or comonomers. In such a combination of different kinds of monomers, the transition temperature of the copolymer is somewhat higher or lower than that of the homopolymer of the N-substituted (meth) acrylamide monomer alone when the comonomer combined therewith is hydrophilic or oleophilic, respectively. It is desirable that the molar fraction of the monomeric units of the general formula (I) in such a copolymer is at least 10% or, preferably, at least 30% or, more preferably, at least 50%. When the molar fraction of the monomeric units derived from a hydrophilic or oleophilic comonomer is too large, the copolymer is highly water-soluble and does not exhibit phase transition in water allover within the temperature range of the solution or the copolymer is no longer soluble in water, respectively.

Examples of the above mentioned hydrophilic comonomers include acrylamide, N-methylolacrylamide, methacrylamide, N-methyl acrylamide, N,N-dimethyl acrylamide and acryloyl morpholine. Examples of the above mentioned oleophilic comonomers include N-n-butyl acrylamide, N-n-butyl methacrylamide, N-sec-butyl acrylamide, N-sec-butyl methacrylamide, N-tert-butyl acrylamide, N-tert-butyl methacrylamide and other N-(long chain alkyl) (meth) acrylamides.

It is preferable in the invention, however, that the thermosensitive polymer consists of the monomeric units of the general formula (I) alone because, as compared with the above mentioned copolymer with other ethylenically unsaturated comonomers, the temperature range from start to completion of the phase transition of the thermosensitive polymer in water is very narrow to give a possibility to exactly control the temperature for vascular embolization depending on the respective particular object of the intravascular surgery.

The polymerization reaction of the N-substituted (meth) acrylamide represented by the general formula (II) either alone or in combination with other copolymerizable monomers to give a homo- or copolymer mainly consisting of the monomeric units of the formula (I) can be performed according to a conventional procedure for the radical polymerization of ethylenically unsaturated monomers including solution polymerization and bulk polymerization, of which solution polymerization is usually preferred. Examples of the solvents used in the solution polymerization include, though not particularly limitative thereto, water, alcohols such as methyl and ethyl alcohols, ketones such as acetone and methyl ethyl ketone, ethers such as tetrahydrofuran and dioxane and aromatic hydrocarbons such as benzene and toluene. These solvents can be used either singly or as a mixture of two kinds or more, if compatible. The concentration of the monomer or monomers in the solution for the solution polymerization is in the range from 0.1 to 90% by weight or, preferably, from 1 to 30% by weight.

The radical polymerization can be initiated by any known method therefor including irradiation with high-energy radiations such as gamma-rays and electron beams, heating in the presence of a radical polymerization initiator and irradiation with light in the presence of a photosensitizer. Examples of suitable radical polymerization initiators include azo compounds such as azobisisobutyronitrile, 2,2-azobis-2,4-dimethyl valeronitrile, azobiscyclohexane carbonitrile, methyl azobisisobutyrate, azobisisobutylamidine hydrochloride and azobiscyanovaleric acid, water-soluble persulfates such as ammonium persulfate and sodium persulfate and organic peroxides such as benzoyl peroxide and cumene hydroperoxide as well as redox-type polymerization initiator systems consisting of a water-soluble persulfate, e.g., ammonium persulfate, and a water-soluble reducing agent, e.g., sodium sulfite. The amount of the radical polymerization initiator is, usually, from 0.01 to 10 parts by weight or, preferably, from 0.05 to 3 parts by weight per 100 parts by weight of the monomer or monomers. The polymerization temperature is, though dependent on the types of the polymerization initiator, in the range, usually, from 10° to 100° C. or, preferably, from 40° to 80° C. It is important that these reaction conditions are selected so that the polymer obtained thereby may have an average degree of polymerization corresponding to an intrinsic viscosity $[\eta]$ of the polymer in a tetrahydrofuran solution at 27° C. in the range from 0.01 to 6.0 dl/g or, preferably, from 0.1 to 2.0 dl/g.

After completion of the polymerization reaction, the thermosensitive polymer formed in the polymerization mixture is isolated therefrom by removing the unreacted monomer as completely as possible by a known isolation and purification procedure such as reprecipitation, dialysis, ultrafiltration and the like because it is known that the N-substituted (meth) acrylamide monomers in general have strong neurotoxicity.

In practicing the method of the invention for vascular embolization, the thus purified thermosensitive polymer is dissolved in water to give an aqueous solution in a concentration in the range from 0.5 to 50% by weight or, preferably, from 1 to 30% by weight for injection into the blood vessel of the patient. When the concentration of the thermosensitive polymer is too low, the coagulate formed from the aqueous solution upon temperature elevation is too soft retaining some flowability so that the effect of vascular embolization would be incomplete. An aqueous solution of which the concentration of the thermosensitive polymer exceeds the above mentioned upper limit can hardly be prepared due to the limited solubility of the polymer in water or, if such a solution could ever be obtained, difficulties are encountered in the injection of the solution into the patient's blood vessel due to the unduly high viscosity of the solution.

In step (a) of the inventive method for vascular embolization, the thus prepared aqueous solution of the thermosensitive polymer is injected through a catheter inserted into the blood vessel of the patient to be subjected to the intravascular surgery. It is of course essential that the aqueous solution of the polymer to be injected is at a temperature substantially lower than the transition temperature of the polymer in the aqueous solution in order to prevent premature coagulation of the solution. After injection into the blood vessel, the solution is warmed by the body temperature of the patient, which is usually about 37° C., to exceed the transition temperature of the thermosensitive polymer in water so that phase transition of the polymer takes place to form a coagulate of the solution which serves as an embolus in the blood vessel. It is of course optional that the affected part including the blood vessel be locally heated from outside so as to accelerate coagulation of the aqueous solution of the thermosensitive polymer injected into the blood vessel.

As is understood from the above given description, the method of the present invention for vascular embolization is advantageous in several respects over conventional methods. Namely, the method is free from the problems of affection due to organic solvents because the embolizing agent injected into the blood vessel is an aqueous solution containing absolutely no organic solvent. The thermosensitive polymer as the effective ingredient in the aqueous solution is also little toxic not to cause detrimental side effects as is illustrated by the toxicity test described below. Needless to say, the aqueous solution of the polymer can easily be sterilized by a conventional method such as autoclaving or filtration through a sterilization filter. Further, the transition temperature of the polymer in water or the coagulation temperature of the aqueous solution can be freely controlled by adequately selecting the types and combinations of the monomers or comonomers to be polymerized. The embolus once formed in the blood vessel by the coagulation of the aqueous solution can be easily re-dissolved by decreasing the temperature of the local part by cooling from outside leaving no aftereffects due to the vascular embolization after the intravascular surgery.

In the following, examples are given to more fully illustrate the method of the invention as preceded by the description of the toxicity test for the thermosensitive polymer as well as a monomer thereof.

TOXICITY TEST

An acute toxicity test was undertaken using mice as the test animals by the intradermic injection of an acrylamide monomer in the form of an ethyl alcohol solution or a copolymer of acrylamide monomers in the form of an aqueous solution.

Thus, each of six a group of 30 mice in five groups was subjected to intradermic injection with an ethyl alcohol solution of N-isopropyl acrylamide in a dose of 30 to 1000 mg/kg varied in five dosage levels and their body weights were measured every day thereafter. As a result of this treatment, four of the six mice belonging to the group of 1000 mg/kg dosage level died within 24 hours from the injection while only one of six mice died within 48 hours from the injection, the other mice surviving thereafter. The mice as died were subjected to autopsy for pathological inspection to find no abnormality excepting a strong inflammation on the portion of the intradermic injection so that the cause of their death could not be defined. A hematological inspection was undertaken for the surviving mice after 7 days and 21 days from the injection along with the autopsy also to find no abnormality.

In view of the above described results in the toxicity test for the acrylamide monomer, similar animal tests were conducted with a copolymer of N-isopropyl acrylamide and N-n-propyl acrylamide having a transition temperature in water of 24.3° C. Thus, each of six a group of 24 mice in four groups was subjected to intradermic injection with an aqueous solution of the polymer in four dosage levels of 250 to 2000 mg/kg as polymer. No death was caused in any of the mice after completion of the test. Absolutely no abnormality could be detected in the hematological inspection and autopsy. A conclusion derived from the above described toxicity test is that the toxicity of the polymer of the acrylamide monomer is very low.

EXAMPLE

Into a glass ampule were taken 0.46 g of N-isopropyl acrylamide, 1.89 g of N-n-propyl acrylamide and 20 ml of a methyl alcohol solution of azobisisobutyronitrile in a concentration of 1 g/liter to form a polymerization mixture which was deaerated by evacuation followed by sealing of the ampule. The thus sealed ampule was kept at 60° C. for 22 hours to effect copolymerization of the acrylamide monomers. The viscosity of the polymerization mixture in the ampule was noticeably increased indicating proceeding of the polymerization reaction. After completion of the polymerization time, the ampule was opened and the polymerization mixture was poured into a large volume of hot water at 60° C. so as to precipitate the copolymer. The intrinsic viscosity $[\eta]$ of the thus obtained copolymer as determined in tetrahydrofuran as the solvent by using a dilution Ubbelohde viscosimeter was 0.25 dl/g at 27° C.

As a measure for the determination of the transition temperature of the copolymer in water, appearance of turbidity in an aqueous solution of the copolymer was examined. Thus, an aqueous solution of the copolymer in a concentration of 1% by weight was subjected to the measurement of light transmission at a wavelength of 500 nm in a spectrophotometer equipped with a temperature controller by varying the temperature at a rate of temperature elevation and lowering of 1° C./minute within a range from a temperature lower than 10° C. up to a temperature exceeding the temperature $T_L$ at which the light transmission was just a half of that at the lowest temperature at which the solution was perfectly clear. The thus determined temperature $T_L$, which was assumed to represent the transition temperature of the copolymer in water, was 24.3° C.

An intravenously anesthetized rabbit was subjected to dissection on the femur to expose the femoral artery into which a microcatheter was inserted and thrusted to reach the artery of the kidney where angiography was to be conducted. Thereafter, a 1 ml portion of a 10% by weight aqueous solution of the above prepared copolymer was introduced into the artery and embolization of the artery of the kidney was confirmed by the angiographical examination. Further, the kidney was extirpated and subjected to formalin fixation in a thermostat at 37° C. to prepare a sectioned tissue preparation, of which a microscopic photograph was taken and is shown in FIG. 1. In this photograph, the areas indicated by "A" are each a section of the artery of the kidney embolized by the coagulate of the polymer solution. The tiny black spots within these areas show red blood cells.

The results of the embolization test by using the artery of the kidney of a rabbit were substantially the same as above when the concentration of the thermosensitive polymer in the aqueous solution was increased to 20% by weight.

What is claimed is:

1. A method for vascular embolization of a blood vessel of a patient which comprises the steps of:

(a) injecting, into the blood vessel of the patient, an aqueous solution containing from 0.5% to 50% by weight of a thermosensitive polymer consisting of the monomeric units comprising a monomeric moiety derived from an N-substituted (meth) acrylamide compound and represented by the general formula $$+CH_2-CR^1(-CO-NR^2R^3)+,$$

in which $R^1$ is a hydrogen atom or a methyl group, $R^2$ is a hydrogen atom, an alkyl group or an alkoxy-substituted alkyl group and $R^3$ is an alkyl group or an alkoxy-substituted alkyl group, having an intrinsic viscosity [η] in the range from 0.01 to 6.0 dl/g in tetrahydrofuran at 27° C. and having a transition temperature for coagulation of the aqueous solution by the phase transition of the polymer into a coagulate within a range from 10° to 37° C., at a temperature lower than the transition therapeutically acceptable temperature; and (b) heating the aqueous solution of the thermosensitive polymer inside of the blood vessel up to a temperature higher than the transition temperature of the thermosensitive polymer either externally or by the body temperature of the patient.

2. The method for vascular embolization of the blood vessel of a patient as claimed in claim 1 in which the molar fraction of the monomeric units derived from the N-substituted (meth) acrylamide compound in the thermosensitive polymer is at least 10%.

3. The method for vascular embolization of the blood vessel of a patient as claimed in claim 1 in which the concentration of the thermosensitive polymer in the aqueous solution is in the range from 1 to 30% by weight.

4. The method for vascular embolization of the blood vessel of a patient as claimed in claim 1 in which the thermosensitive polymer has an intrinsic viscosity [η] in the range from 0.1 to 2.0 dl/g in tetrahydrofuran at 27° C.

5. The method of claim 1, wherein the monomeric moiety is a mixture of N-isopropyl acrylamide and N-n-propyl acrylamide.

* * * * *

UNITED STATES PATENT AND TRADEMARK OFFICE
CERTIFICATE OF CORRECTION

PATENT NO. : 5,525,334
DATED : June 11, 1996
INVENTOR(S) : Shoji ITO et al.

It is certified that error appears in the above-indentified patent and that said Letters Patent is hereby corrected as shown below:

Claim 1, column 9, line 18, delete "therapeutically acceptable"; and column 9, line 21, before "temperature" insert --therapeutically acceptable--.

Signed and Sealed this

Eighth Day of October, 1996

*Attest:*

BRUCE LEHMAN

*Attesting Officer*     *Commissioner of Patents and Trademarks*